United States Patent
Ding et al.

(10) Patent No.: US 9,163,230 B2
(45) Date of Patent: Oct. 20, 2015

(54) CHROMATOGRAPHY COLUMN AND METHOD FOR ISOLATING NUCLEIC ACID

(71) Applicants: Shaofeng Ding, Santa Fe Springs, CA (US); Qiang Liu, Upland, CA (US)

(72) Inventors: Shaofeng Ding, Santa Fe Springs, CA (US); Qiang Liu, Upland, CA (US)

( * ) Notice: Subject to any disclaimer, the term of this patent is extended or adjusted under 35 U.S.C. 154(b) by 255 days.

(21) Appl. No.: 13/918,979

(22) Filed: Jun. 16, 2013

(65) Prior Publication Data
US 2014/0179908 A1    Jun. 26, 2014

Related U.S. Application Data

(60) Provisional application No. 61/701,486, filed on Sep. 14, 2012.

(51) Int. Cl.
| | |
|---|---|
| *C07H 21/00* | (2006.01) |
| *C07H 21/02* | (2006.01) |
| *C07H 21/04* | (2006.01) |
| *C12N 15/10* | (2006.01) |

(52) U.S. Cl.
CPC .............. *C12N 15/101* (2013.01); *C07H 21/00* (2013.01); *C07H 21/02* (2013.01); *C07H 21/04* (2013.01)

(58) Field of Classification Search
None
See application file for complete search history.

(56) References Cited

PUBLICATIONS

Takahashi et al., "Automated Tandem High-Performance Liquid Chromatographic System for Separation of Extremely Complex Peptide Mixtures" Journal of Chromatography (1985) vol. 326 pp. 407-418.*
Comparison Guide to C18 Reversed Phase HPLC Columns, Fourth Edition Jun. 2008, published by MAC-MOD Analytical.*
Green et al., "A New Scalable Method for the Purification of Recombinant Adenovirus Vectors" Human Gene Therapy (2002) vol. 13 pp. 1921-1934.*
Purdy et al., "Rapid Extraction of DNA and rRNA from Sediments by a Novel Hydroxyapatite Spin-column Method" (1996) vol. 62 No. 10 pp. 3905-3907.*

* cited by examiner

*Primary Examiner* — Eric Olson (57) ABSTRACT

The present invention provides a chromatography column and a method for isolating nucleic acid molecules. In one embodiment, the present invention provides a double-layer column of a first anion exchange membrane and a second serially coupled silica membrane. Upon flowing a nucleic acid-containing solution through the first anion exchange membrane, the nucleic acid binds to and then elutes from the first membrane. The eluted solution then flows serially through the second silica membrane, which the nucleic acid binds to and then elutes from. Due to this novel serial coupled double-layer principle, the present invention is particularly suitable for co-isolating RNA and DNA, for isolating nucleic acid embraced by proteins, e.g., viruses, and for isolating diluted nucleic acid in a large volume, e.g., plasma. In addition, the eluted nucleic acid is ready for downstream applications.

18 Claims, 4 Drawing Sheets

CHROMATOGRAPHY COLUMN AND METHOD FOR ISOLATING NUCLEIC ACID

CROSS-REFERENCE TO RELATED APPLICATIONS

This application claims priority from U.S. provisional patent application Ser. No. 61/701,486 filed on Sep. 14, 2012.

SEQUENCE LISTING

This application is being filed along with a Sequence Listing and its electronic format entitled SequenceListing.txt.

BACKGROUND

The present invention relates to a chromatography column and a method for isolating nucleic acid. It is particularly suitable for co-isolating RNA and DNA, for isolating nucleic acid contained in a particle, e.g., virus, and for isolating diluted nucleic acid in a large volume, e.g., plasma.

Nucleic Acid Isolation

Nucleic acid isolation is an important step for many biochemical and diagnostic uses, e.g., cloning, transformation, restriction digestion, in vitro transcription, amplification, sequencing. However, it can not be easily carried out because of the presence of large amounts of cellular and other contaminants, e.g., proteins, carbohydrates, and small metabolites in crude samples. Thus, simple, fast, efficient, reliable, and cost-effective methods are needed.

Silica-Based Isolation

The silica- or silicon dioxide-based method has become a popular method for isolating nucleic acid that use controlled pore glass, filters embedded with silica particles, silica gel particles, resins comprising silica in the form of diatomaceous earth, and glass fibers[1 2 3 4 5 6 7 8 9]

The basic procedure is simple. DNA or RNA is bound to the surface of silica resin or membrane in the presence of a high concentration of chaotrophic salts, contaminants are washed away, and DNA is eluted in water or low-salt buffer.

The principle of silica-based isolation is based on the high affinity of the negatively charged DNA backbone towards the positively charged silica surface[10] under concentrated chaotrophic salt conditions, e.g., sodium iodide (NaI), sodium perchlorate ($NaClO_4$), guanidinium hydrochloride (GuHCl), and guanidinium thiocyanate (GuTC).

The effects of ionic strength, temperature, pH, DNA size and conformation on the binding of nucleic acid to the silica surface were investigated[11]. For example, the binding capacity of the silica surface is linearly related to the chaotrophic salt concentration. Additionally, at a given chaotrophic salt concentration, the binding capacity to the silica surface of any type of DNA is higher at a lower pH value.

GuTC and GuHCl are commonly used for binding nucleic acid to the silica surface. NaI and $NaClO_4$ are also used to a lesser extent. GuTC at a concentration of 4 M to 6 M works best, while GuHCl is used at a higher concentration of 6 M. The binding efficiency is significantly improved in the presence of ethanol or propanol. In order to control the pH value of the binding reagent, sodium acetate and Tris-HCl buffers, ranging from pH 6 to 7.5 are often used. Moreover, guanidinium salts, e.g., GuTC, are known to efficiently lyse cells and denature proteins[4], eliminating the need for adding denaturing enzymes, e.g., proteinase.

Spin and vacuum chromatography columns are commonly used within which silica resin or membrane is packed as the stationary phase, e.g., those of PureYield plasmid midiprep system and WizardPlus minipreps DNA purification system from Promega, QIAprep miniprep kit from Qiagen, and EZgene plasmid purification miniprep kit from Bioland.

The silica-based method provides a quick, convenient, and efficient method. The purified DNA is qualified and ready to use for a wide variety of downstream applications. However, the starting volume of samples, e.g., plasma, is limited because up to 3 volumes of chaotrophic salt solution should be added to one volume of the DNA or RNA samples to reach the effective chaotropic salt concentration required by silica binding.

Anion Exchange-Based Isolation

The method of anion exchange resin and membrane is also commonly used for isolating nucleic acid. In this procedure, DNA is bound to the anion exchanger in the presence of a low salt concentration at a low pH. DNA is eluted in the presence of a high salt concentration at a high pH value[12 13 14 15 16 17 18 19 20 9].

The binding principle is based on the interaction between the negatively charged phosphates of the DNA backbone and the positively charged group, e.g., DEAE, on the surface. The salt concentration and pH value of a solution used determine whether DNA is bound or eluted.

Anion exchange bead-based columns, often gravity flow driven, are common, e.g., QIAGEN genomic-tips kit. The QIAGEN resin contains porous silica bead as support coated with diethylaminoethanol (DEAE) functional group. Others include Pall AcroSep chromatography columns with DEAE weak anion exchange ceramic HyperD F bead and with Q strong anion exchange ceramic HyperD F bead.

In contrast to the bead-based columns, anion exchange membrane columns, often spin or vacuum flow driven, are available. They have the advantages of high flow rate, low cost, and high throughput, e.g., Vivapure weak anion exchange mini D membrane spin column and Vivapure strong anion exchange mini Q membrane spin column[21].

Anion exchange columns provide an easy, safe, and reliable method for the isolation of nucleic acid from various types of samples. The prepared nucleic acid is of superior purity equivalent to two rounds of purification on CsCl gradient centrifuge. However, the eluted nucleic acid is not ready to use because of the high salt concentration in the elution buffer. An extra step of ethanol or isopropanol precipitation is typically needed to remove the salt.

Advantage of the this Invention

We provide a chromatography column and a method that removes the drawbacks of the silica-based isolation and Anion exchange-based isolation of nucleic acid.

Because of a new principle of double-layer chromatography, the chromatography column and method is particularly suitable for co-isolating RNA and DNA, for isolating nucleic acid embraced by proteins, e.g., viruses, and for isolating a little amount of nucleic acid in a large volume, e.g., plasma. In addition, the eluted nucleic acid is ready for downstream applications.

SUMMARY OF THE INVENTION

A new method for isolating nucleic acid with a novel principle was developed, comprising: a) providing a chromatography column comprising a first solid layer and a second solid layer which are serially coupled so that solutions flow through the first layer and then through the second layer, b) flowing a first aqueous solution containing nucleic acid through the first layer to which the nucleic acid becomes bound, c) flowing a second aqueous solution through the first layer and eluting the bound nucleic acid, and then through the second layer to which the eluted nucleic acid becomes bound, and d) flowing a third aqueous solution through the second layer and eluting the bound nucleic acid.

The nucleic acid can be either DNA or RNA, and it can be embraced by proteins, e.g., those of viruses.

The first solid layer is composed of an anion exchange medium, either membrane-based or bead-based. Anion exchangers of the anion exchange medium can be selected from the group consisting of Diethylamine (D or DEAE), Quaternary ammonium (Q), and Diethylaminopropyl (ANX).

The second solid layer is composed of a silica membrane or silica bead.

The first solution comprises a low salt concentration at a low pH value, e.g., 20 mM Tris-HCl, pH 6.0-8.0, so that the nucleic acid is bound to the first layer.

The second solution comprises chaotropic salt at a high concentration so that the nucleic acid is eluted from the first layer and then is bound to the second layer. The chaotropic salt can be selected from the group consisting of GuTC, GuHCl, NaI, and NaClO$_4$. The chaotropic salt concentration can range from 2 to 8 M. The second solution can also comprise other salts, like NaCl and KCl, to increase ion strength. In addition, the second solution can contain ethanol or isopropanol.

The third solution comprises a low salt concentration at a high pH value, e.g., 10 mM Tris-HCl, 0.1 mM EDTA, pH 8.0-9.0, so that the bound nucleic acid is eluted from the second layer.

In addition, the method can further comprise a step between steps b and c: flowing an aqueous solution BC, e.g., 10 mM Tris-HCl, pH 6.0-8.0, to wash contaminants of proteins, carbohydrates, and small metabolites from the first layer.

Furthermore, the method can further comprise a step between steps c and d: flowing an aqueous solution CD, e.g., a 2 to 8 M chaotropic salt concentration, to wash contaminants of proteins, carbohydrates, and small metabolites from the second layer. The solution CD can be composed of the same as the second solution, or the solution CD can be made up differently, e.g., 10 mM Tris-HCl, 80% ethanol, pH 7.5.

The invention can also be described as a double-layer chromatography column for isolating nucleic acid, comprising: a) a first solid layer, to which nucleic acid becomes bound when a first aqueous solution containing nucleic acid flows through, and from which the bound nucleic acid is eluted when a second aqueous solution flows through, and b) a second solid layer, to which the eluted nucleic acid becomes bound when the second aqueous solution flows through, and from which the bound nucleic acid is eluted when a third aqueous solution flows through. In such a way, the solutions flow through the first layer and then through the second layer, thus the first layer is serially coupled to the second layer.

BRIEF DESCRIPTION OF THE DRAWINGS

FIG. 1 shows a schematic of the double-layer chromatography column. In the example shown, a first solid layer is an anion exchange membrane, e.g., DEAE, and a second solid layer is a silica membrane, which are serially coupled in the order. Solutions flow through the first layer and then through the second layer.

FIG. 2 shows the isolation process within the double layers. The first solid layer of DEAE membrane and the second solid layer of silica membrane are examples. Solutions flow through the DEAE membrane and then through the silica membrane, indicated by arrows. The nucleic acid, indicated by double curved lines, is bound to and then eluted from the DEAE membrane, depending on the first or the second solution. Then eluted nucleic acid is bound to and then eluted from the silica membrane, again depending on the second or the third solution.

DETAILED DESCRIPTION OF THE INVENTION

Principle and Procedure

Figure 1:
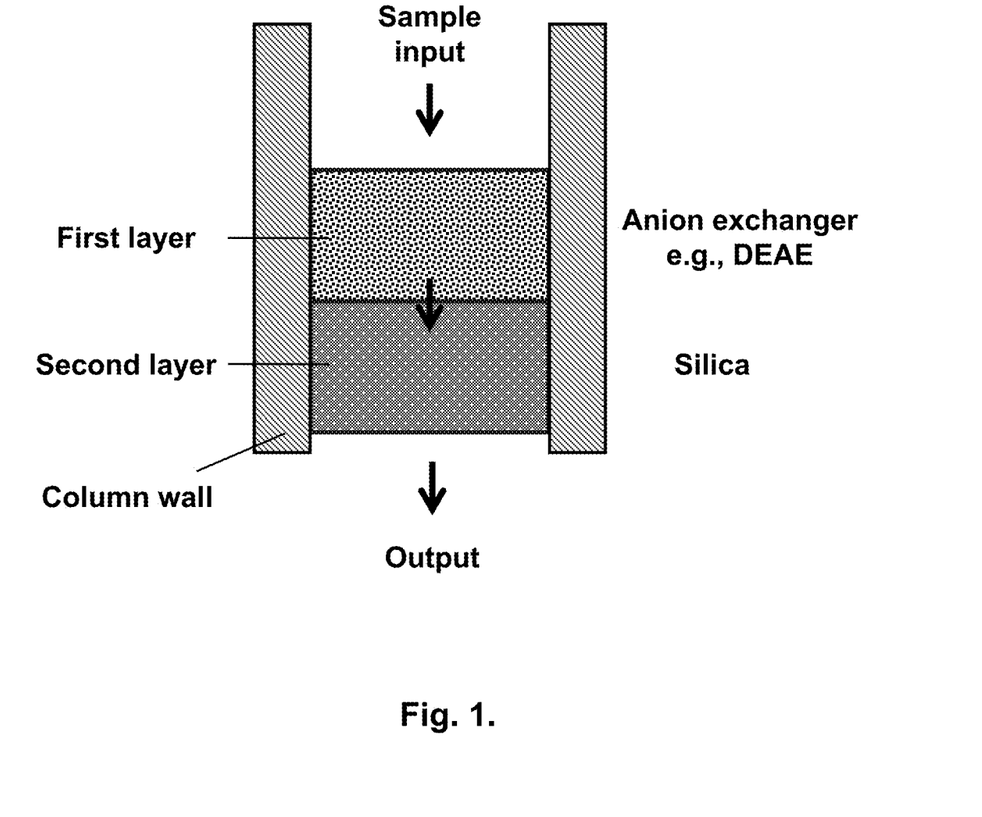

In one aspect, the present invention is a double-layer chromatography column for isolating nucleic acid. It comprises at least two different solid layers of the first anion exchange medium, e.g., a DEAE anion exchange membrane, and the second silica medium, e.g., a silica membrane (FIG. 1). Solutions flow through the first layer and then through the second layer.

The flow may be driven by vacuum or centrifuge.

Figure 2:
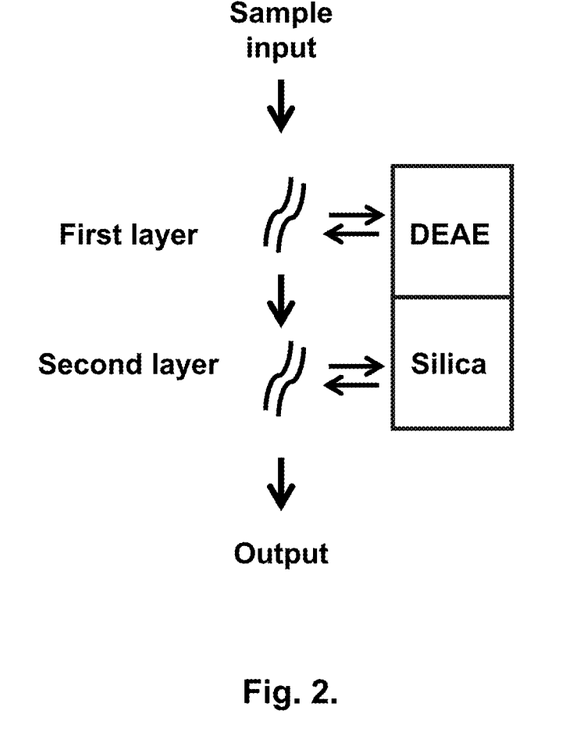

When a first solution containing nucleic acid flows through the first layer, the nucleic acid becomes bound (FIG. 2).

When a second solution flows through the first layer to which the nucleic acid is bound, the bound nucleic acid is eluted. When it flows through the second layer, the eluted nucleic acid becomes bound. In this sense, the second solution functions as a "serial coupler", i.e., eluting the nucleic acid from the first layer and then binding the nucleic acid to the second layer.

When a third solution flows through the second layer to which the nucleic acid is bound, the nucleic acid becomes eluted.

The Composition of the Double Layers

Anion Exchange Membrane or Bead in the First Solid Layer

The anion exchange membrane or bead comprises a supporting matrix and a covalently attached anion exchanger. Weak anion exchanger of Diethylamine (D, or DEAE), strong anion exchanger of Quaternary ammonium (Q), and another weak anion exchanger of Diethylaminopropyl (ANX) can be used (Table 1).

TABLE 1

Functional group of anion exchangers in the first layer

| Anion exchanger | Ionic group | Type | Working pH | pKa |
|---|---|---|---|---|
| Diethylamine (D, or DEAE) | R—CH$_2$N$^+$H(CH$_2$H$_5$)$_2$ | Weak anion exchanger | pH 4-10 | 9.5 |
| Quaternary ammonium (Q) | R—CH$_2$N$^+$(CH$_3$)$_3$ | Strong anion exchanger | pH 2-12 | 11 |
| Diethylaminopropyl (ANX) | R—CH$_2$CHOHCH$_2$N$^+$H(CH$_2$CH$_3$)$_2$ | Weak anion exchanger | pH 4-10 | |

Many types of anion exchange bead and membrane are available, including Waterman DEAE anion exchange cellulose membrane (DE81 paper), Vivapure DEAE anion exchange regenerated cellulose membrane used in Vivapure IEX D spin column, Vivapure Q anion exchange regenerated cellulose membrane used in Vivapure IEX Q spin column, Pall Mustang Q anion exchange cross-linked polymeric membrane used in Acrodisc chromatography unit, Pall DEAE Ceramic HyperD F bead used in AcroSep column, Qiagen DEAE anion exchange bead with supporting matrix of silica bead, GE DEAE sepharose bead, GE Q sepharose bead, and GE ANX sepharose bead.

We tested Waterman DEAE anion exchange cellulose membrane (DE81 paper). The binding principle is based on the interaction between the negatively charged phosphates of the DNA backbone and the positively charged group, e.g., DEAE, on the surface. The salt concentration and pH value of a solution used determine whether DNA is bound or eluted. DNA is bound to the anion exchanger surface in the presence of a low salt concentration at a low pH value, e.g., 10 mM Tris-HCl, 1 mM EDTA, pH 7.5, which was used as the first solution in tested examples. DNA is eluted in the presence of a high salt concentration at a high pH value, e.g., 4 M GuTC, 0.5 M NaCl, 20 mM Tris-HCl, pH 7, which was used as the second solution in tested examples.

Silica Membrane or Bead in the Second Solid Layer

The silica membrane or bead can be made of controlled pore glass, filters embedded with silica particles, silica gel particles, resins comprising silica in the form of diatomaceous earth, and glass fibers.

We tested a silica membrane from EZgene plasmid purification miniprep kit of Bioland. Other examples include silica bead and membrane used in PureYield plasmid midiprep system from Promega, Wizard plus minipreps DNA purification system from Promega, and QIAprep miniprep kit from Qiagen.

The binding principle is based on the high affinity of the negatively charged DNA backbone to the positively charged silica surface under concentrated chaotrophic salt conditions, e.g., 4 M GuTC, 0.5 M NaCl, 20 mM Tris-HCl, pH 7, which was used as the second solution in tested examples. DNA is eluted in the presence of a high salt concentration at a high pH value, e.g., 10 mM Tris-HCl, 0.1 mM EDTA, pH 9.0, which was used as the third solution in tested examples.

The Aqueous Solutions

The first aqueous solution facilitates the nucleic acid to bind to the first layer. A solution of a low salt concentration at a low pH value, e.g., 10 mM Tris-HCl, 1 mM EDTA, pH 7.5, may be used.

The second aqueous solution facilitates the nucleic acid to be eluted from the first layer and to be bound to the second layer. It may contain 3 M to 6 M GuTC, 20 mM Tris-HCl, pH 6.0-7.5. Other chaotropic salts, e.g., GuHCl, NaI, and $NaClO_4$, can also be used. In addition, chaotropic salts can be used in the presence of organic solvents, e.g., ethanol or isopropanol. Furthermore, the second solution can also comprise other salts, like NaCl and KCl, to increase ion strength, e.g., 4 M GuTC, 0.5 M NaCl, 20 mM Tris-HCl, pH 7.

The third aqueous solution facilitates the nucleic acid to be eluted from the second layer. A solution of a low salt concentration at a high pH value, e.g., 10 mM Tris-HCl, 0.1 mM EDTA, pH 8.0-9.0, may be used.

In addition, between the first solution and the second solution, an aqueous solution BC can flow for washing the first layer that may comprise the same components as the first solution except for the nucleic acid, e.g., 10 mM Tris-HCl, 1 mM EDTA, pH 7.5, which was used in tested example. Furthermore, between the second solution and the third solution, an aqueous solution CD can flow for washing the second layer. The solution CD can be composed of the same as the second solution, or the solution CD can be made up differently, e.g., 10 mM Tris-HCl, 80% ethanol, pH 7.5, which was used in tested examples.

The Nucleic Acid

We tested 1 kb DNA marker and human genomic DNA. However, the nucleic acid(s) may be DNA and RNA in any possible configuration, e.g., in the forms of linear, circular, double-stranded, and single-stranded.

The nucleic acid(s) may be contained in a particle, e.g., virus. In this case, the pH value of the first solution containing the virus can be adjusted to make the embraced proteins negatively charged, and thus the proteins is bound to the first layer. Driven by centrifuge or vacuum, a little volume of the first solution is retained on and within the first layer. When the second solution containing as high as 6 M GuTC is added to the first layer, the resulting guanidinium salt will not be diluted too much by the little volume of the retained first solution. Therefore, the concentrated guanidinium salt is able to lyse the particle on the first layer, making the nucleic acid released. Thus, the first layer functions as a "binder", a "concentrator" and a "lyser".

DNA and RNA can be isolated together due to the "binder" and "concentrator" functions of the first layer. The resulting high concentration of guanidinium salt can make the DNA and RNA efficiently bound to the second layer.

A little amount of nucleic acid in a large volume of sample, e.g., plasma, can be isolated due to the "binder" and "concentrator" functions of the first layer, as described above.

Example 1

Materials and Methods

DNA Marker, Silica Membrane Column, and DEAE Membrane 1 kb DNA marker was from BioLabs that contains 10 double-stranded DNA fragments of 0.5, 1, 1.5, 2, 3, 4, 5, 6, 8, and 10 kilobases (kb). The silica membrane column was from Bioland EZgene plasmid purification miniprep kit. Whatman DE81 cellulose chromatography paper, a DEAE membrane, was from GE Healthcare.

Preparation of Human Genomic DNA

Genomic DNA was extracted from blood white cells and stored in 10 mM Tris-HCl (pH 8.0) and 1 mM EDTA buffer using DNeasy mini blood and tissue kit according to the manufacturer's protocol (Qiagen). The concentration was measured by a spectrophotometer at 260 nm. It was stored at −20° C. until used.

Example 2

The Chromatography Column and Method for Isolating Nucleic Acid

Preparation of DEAE Membrane and Silica Membrane Double-Layer Column

Figure 3:
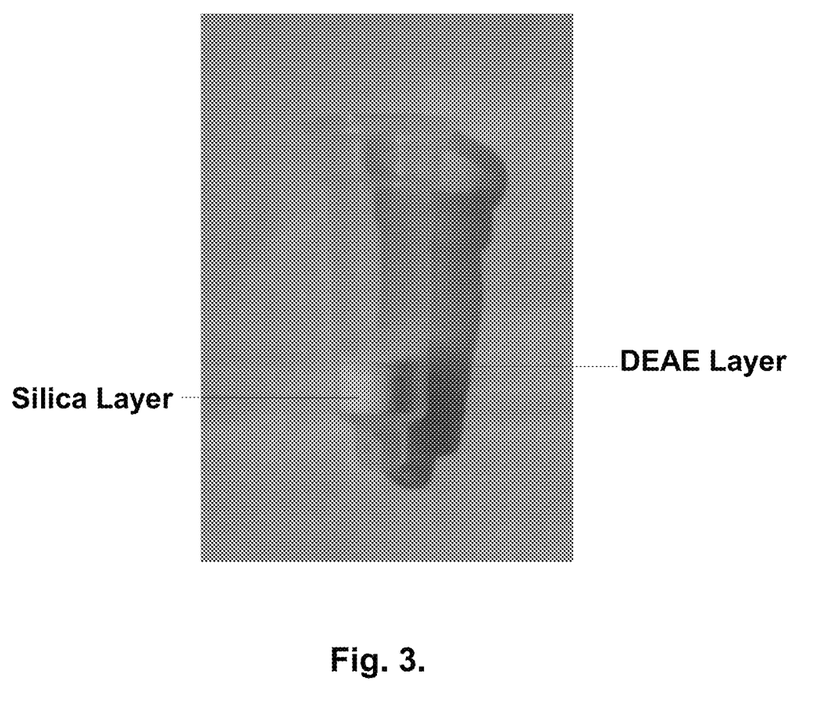
FIG. 3 shows a sample of the double-layer chromatography column. The first solid layer is a DEAE membrane composed of five sheets of Whatman DE81 paper assembled and the second solid layer is a silica membrane (7 mm diameter).

Whatman DE81 paper was cut into disks with diameter of 7 mm. Five such disks were assembled and put on the top of the silica membrane that was already installed in the spin column (FIG. 3). Thus, the double-layer column was prepared and used for isolating nucleic acid.

Isolation of the 1 Kb DNA Marker and Human Genomic DNA

Using the double-layer column, we tested the human genomic DNA and 1kb DNA marker.

200 μl of the first solution (10 mM Tris-HCl, 1 mM EDTA, pH 7.5) containing 2.5 μg of the 1 kb DNA marker and 2.5 μg of genomic DNA was transferred into each column and centrifuged at 8,000 rpm for 2 minutes. The filtrate was discarded.

For washing, 400 μl of 1×TE buffer (10 mM Tris-HCl, 1 mM EDTA, pH 7.5) was added into each column and centrifuged at 10,000 rpm for 1 minute. The filtrate was discarded.

600 μl of the second solution was added into each column. Four guanidine salt conditions were examined: 1) 4 M GuTC, 0.5 M NaCl, 20 mM Tris-HCl, pH 7; 2) 3.6 M GuTC, 1 M NaCl, 20 mM Tris-HCl, pH 7; 3) 3 M GuTC, 2 M NaCl, 20 mM Tris-HCl, pH 7; and 4) 3.6 M GuHCl, 0.5 M NaCl, 20 mM Tris-HCl, pH 7. The columns were centrifuged at 10,000 rpm for 1 minute. The filtrate was discarded For washing, 600 μl of wash buffer (10 mM Tris-HCl, 80% ethanol, pH 7.5) was added into each column and centrifuged at 10,000 rpm for 1 minute. The filtrate was discarded.

100 μl of the third solution (10 mM Tris-HCl, 0.1 mM EDTA, pH 9.0) was added into each column and centrifuged at 13,000 rpm for 1 minute. The filtrate was collected as output.

Spectrophotometery to Measure the Collected DNA Quantity

The concentration of the collected DNA in TE buffer (10 mM Tris-HCl, 0.1 mM EDTA, pH 9.0) was measured by a spectrophotometer at 260 nm and 280 nm (Table 2). With 4 M GuTC, 0.5 M NaCl, 20 mM Tris-HCl, pH 7, as the second solution, the total amount of DNA was collected the most, showing the effect of guanidine salt conditions.

TABLE 2

DNA recovery rates with four guanidine salt conditions

| | Guanidine salt conditions [c] | | | |
|---|---|---|---|---|
| | 1 | 2 | 3 | 4 |
| Total input [a] | 5.0 μg | 5.0 μg | 5.0 μg | 5.0 μg |
| Total amount of DNA collected [b] | 1.7 μg | 1.4 μg | 1.5 μg | 0.88 μg |
| Recovery rates | 33.1% | 28.0% | 30.0% | 17.7% |

[a] It contained 2.5 μg of the 1 kb DNA marker and 2.5 μg of genomic DNA.
[b] It contained the 1 kb DNA marker and genomic DNA collected in 100 μl of the third solution, and its total amount was determined by the spectrophotometer at 260 nm.
[c] The four guanidine salt conditions were 1) 4M GuTC, 0.5M NaCl, 20 mM Tris-HCl, pH 7; 2) 3.6M GuTC, 1M NaCl, 20 mM Tris-HCl, pH 7; 3) 3M GuTC, 2M NaCl, 20 mM Tris-HCl, pH 7; and 4) 3.6M GuHCl, 0.5M NaCl, 20 mM Tris-HCl, pH 7.

Agarose Gel Electrophoresis to Measure the Collected DNA Sizes

Figure 4:
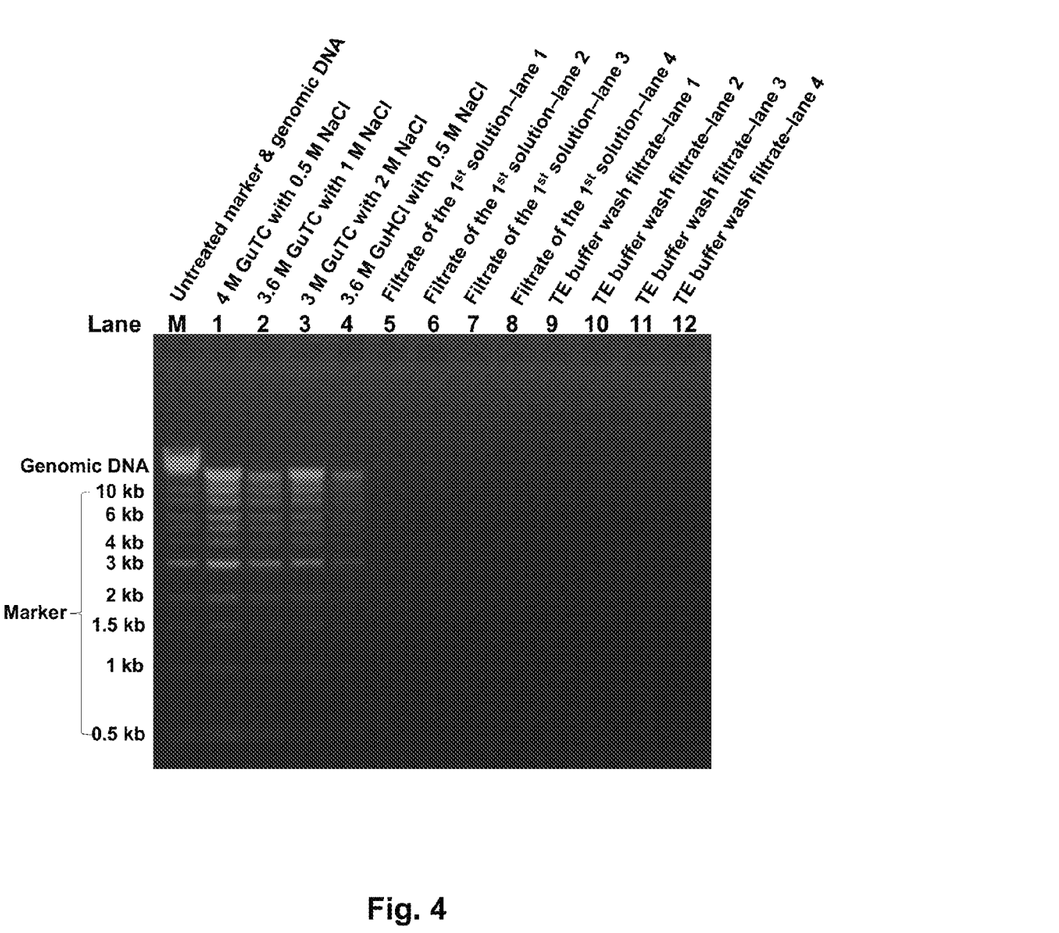
FIG. 4 shows a 1% agarose gel to measure the sizes of the isolated 1 kb DNA marker and human genomic DNA. Lane M is the untreated 1 kb DNA marker and genomic DNA mix as control. Lanes 1 to 4 are the eluted 1 kb DNA marker and human genomic DNA with different conditions of the second solution. Lanes 5 to 8 are the filtrates of the first solution. Lanes 9 to 12 are the filtrates of the 1×TE washing buffer.

50 μl of the collected DNA sample eluted from the third solution was electrophoresed through a standard 1% agarose gel (FIG. 4). For comparison, the filtrates of the first solution (50% of the amount) and the filtrates of 1×TE washing buffer (50% of the amount) were also loaded. The gel was stained with ethidium bromide for UV photography by a charge-coupled device camera.

Compared with the band patterns of the untreated 1 kb DNA marker and genomic DNA on the agarose gel, the treated DNA bands showed consistent intensities under each of the four guanidine salt conditions, suggesting high quality.

In addition, the filtrates of the first solution and the filtrates of 1×TE washing buffer did not show any observable bands, suggesting the 1 kb DNA marker and genomic DNA in the first solution were bound to the Whatman DE81 paper and could not be washed away by the 1×TE washing buffer.

Furthermore, to show the necessity of the DEAE membrane in the double-layer column, a column only with the silica membrane (single-layer) was tested under the same conditions. There was virtually no any DNA collected in the third solution. Thus, both layers are needed for the isolation.

Example 3

Application to Real-Time PCR

Preparation of Primers

The primers were synthesized by Integrated DNA Technologies (Table 3).

TABLE 3

List of primers for PCR

| Name [a] | Sequence (5' to 3') (SEQ ID NO: | Location | Product size (bp) | Starting template |
|---|---|---|---|---|
| P53(13280)20D | AGGGTCCCCAGGCCTCTGAT (1) | Intron 5 | 208 | Human genomic |
| P53(13488)22U | GCCACTGACAACCACCCTTAAC (2) | Intron 6 | | DNA |

[a] For example, P53 means the human P53 gene; (13280), 5' end of the primer begins at nucleotide 13280 according to GenBank accession: x54156; D, downstream (i.e., in the direction of transcription). The precise sizes and locations of the PCR fragment can be obtained from the informative names.

Real-Time PCR Assay

The primers were designed to amplify a 209-bp region of exon 6 of the P53 gene. Each PCR mixture contained a total volume of 25 μl: 50 mM KCl, 10 mM Tris-HCl (pH 8.3), 1.5 mM $MgCl_2$, 200 μM each dNTP, 0.1 μM each primer for the human P53 gene, 0.1× Sybr Green I dye, 0.02% Twee-20, 0.02% NP-40, 50 ng of total DNA, and 1 U of Taq polymerase.

A Bio-Rad CFX96 real time PCR detection system was used for quantification of the amplified product. Analysis mode: SybrGreen fluorophore, Baseline setting: baseline subtracted curve fit, Threshold cycle (Ct) determination: single threshold, Baseline method: SYBR auto calculated, Threshold setting: auto calculated.

The cycling entailed denaturation at 94° C. for 15 seconds, annealing at 55° C. for 30 seconds, and elongation at 72° C. for 1 minute for 30 cycles. Before thermocycling, a step of 94° C. for 2 minutes was applied to completely denature the genomic DNA.

After the last cycle, melting curving analysis was followed from 68° C. to 95° C. with increment 0.5° C. and holding 5 seconds.

We examined the untreated and the four differently treated DNA samples using real-time PCR. The amplification results showed similar efficiencies among them (Ct=23±1 cycles). In addition, in melting curving analysis, only $T_m$ 84.5±0.5° C. was showed from the amplified products. Thus, the eluted nucleic acid can be directly used for amplification without further treatment.

REFERENCE

1. Vogelstein, B., and Gillespie, D. (1979). Preparative and analytical purification of DNA from agarose. Proceedings of the National Academy of Sciences of the United States of America 76, 615-619.
2. Chen, C. W., and Thomas, C. A., Jr. (1980). Recovery of DNA segments from agarose gels. Analytical biochemistry 101, 339-341.
3. Marko, M. A., Chipperfield, R., and Birnboim, H. C. (1982). A procedure for the large-scale isolation of highly purified plasmid DNA using alkaline extraction and binding to glass powder. Analytical biochemistry 121, 382-387.
4. Boom, R., Sol, C. J., Salimans, M. M., Jansen, C. L., Wertheim-van Dillen, P. M., and van der Noordaa, J. (1990). Rapid and simple method for purification of nucleic acids. Journal of clinical microbiology 28, 495-503.
5. Boom, R., Sol, C., Beld, M., Weel, J., Goudsmit, J., and Wertheim-van Dillen, P. (1999). Improved silica-guanidiniumthiocyanate DNA isolation procedure based on selective binding of bovine alpha-casein to silica particles. Journal of clinical microbiology 37, 615-619.
6. Tian, H., Huhmer, A. F., and Landers, J. P. (2000). Evaluation of silica resins for direct and efficient extraction of DNA from complex biological matrices in a miniaturized format. Analytical biochemistry 283, 175-191.
7. Breadmore, M. C., Wolfe, K. A., Arcibal, I. G., Leung, W. K., Dickson, D., Giordano, B. C., Power, M. E., Ferrance, J. P., Feldman, S. H., Norris, P. M., et al. (2003). Microchip-based purification of DNA from biological samples. Analytical chemistry 75, 1880-1886.
8. Padhye, V. V., York, C., and Burkiewicz, A. (1997). Nucleic acid purification on silica gel and glass mixtures. U.S. Pat. No. 5,658,548.
9. Smith, C. E., Holmes, D. L., Simpson, D. J., Katzenhendler, J., Bitner, R. M., and Grosch, J. C. (2002). Mixed-bed solid phase and its use in the isolation of nucleic acids. U.S. Pat. No. 6,376,194.
10. Thompson, J. D., Cuddy, K. K., Haines, D. S., and Gillepsie, D. (1990). Extraction of cellular DNA from crude cell lysate with glass. Nucleic acids research 18, 1074.
11. Melzak, K. A. S., C. S. Turner, R. F. B. Haynes, C. A. (1996). Driving Forces for DNA Adsorption to Silica in Perchlorate Solutions. J Colloid and Interface Science 181, 635-644.
12. Ion Exchange Chromatography and Chromatofocusing: Principles and Methods, GE Healthcare. http://wwwgelifesciencescom/gehcls_images/GELS/Related %20Content/Files/13 14823637792/ litdoc11000421AB_20110901010317pdf.
13. Teeters, M. A., Conrardy, S. E., Thomas, B. L., Root, T. W., and Lightfoot, E. N. (2003). Adsorptive membrane chromatography for purification of plasmid DNA. Journal of chromatography A 989, 165-173.
14. Endres, H. N., Johnson, J. A., Ross, C. A., Welp, J. K., and Etzel, M. R. (2003). Evaluation of an ion-exchange membrane for the purification of plasmid DNA. Biotechnology and applied biochemistry 37, 259-266.
15. Zhang, S., Krivosheyeva, A., and Nochumson, S. (2003). Large-scale capture and partial purification of plasmid DNA using anion-exchange membrane capsules. Biotechnology and applied biochemistry 37, 245-249.
16. Stadler, J., Lemmens, R., and Nyhammar, T. (2004). Plasmid DNA purification. The journal of gene medicine 6 Suppl 1, S54-66.
17. Yang, Y., Hebron, H. R., and Hang, J. (2008). High performance DNA purification using a novel ion exchange matrix. Journal of biomolecular techniques: JBT 19, 205-210.
18. Smith, C. E., Holmes, D. L., Simpson, D. J., Katzenhendler, J., Bitner, R. M., and Grosch, J. C. (2001). pH dependent ion exchange matrix and method of use in the isolation of nucleic acids. U.S. Pat. No. 6,310,199
19. Skagestad, V. (2011). Nucleic acid extraction method U.S. Pat. No. 8,067,579
20. Kutner, R. H., Puthli, S., Marino, M. P., and Reiser, J. (2009). Simplified production and concentration of HIV-1-based lentiviral vectors using HYPERFlask vessels and anion exchange membrane chromatography. BMC biotechnology 9, 10.
21. Ashby, M. K. M., C. W. Rapid Purification of High Molecular Weight Bacterial Chromosomal DNA using the Vivapure 500 and Vivapure 20-D anion exchange membrane devices. Vivascience application note http://sartoriusorkr/Vivascience/Application_Notes/pdf/ASH_IE_0124pdf.

What is claimed is:

1. A method for isolating nucleic acid, comprising:
   a) providing a chromatography column comprising a first solid layer and a second solid layer which are serially coupled so that solutions flow through the first layer and then the second
   b) flowing a first aqueous solution containing nucleic acid through the first layer to which the nucleic acid becomes bound,
   c) flowing a second aqueous solution through the first layer and eluting the bound nucleic acid, and then flowing the eluted solution through the second layer to which the eluted nucleic acid becomes bound, wherein the second solution comprises chaotropic salt selected from the group consisting of guanidinium thiocyanate, guanidinium hydrochloride, sodium iodide, and sodium perchlorate, and
   d) flowing a third aqueous solution through the second layer and eluting the bound nucleic acid.

2. The method of claim 1, wherein the chaotropic salt concentration is ≥2 M.

3. The method of claim 1, wherein the first solid layer comprises anion exchange membrane or bead.

4. The method of claim 3, wherein the anion exchange membrane or bead is made of anion exchangers selected from the group consisting of Diethylamine (D, or DEAF), Quaternary ammonium (Q), and Diethylaminopropyl (ANX).

5. The method of claim 1, wherein the second solid layer comprises silica membrane or bead.

6. The method of claim 1, wherein the first solution has 100 mM salt concentration.

7. The method of claim 1, wherein the first solution has pH 5.0-8.0.

8. The method of claim 1, wherein the second solution comprises NaCl or KCl.

9. The method of claim 1, wherein the second solution comprises ethanol or isopropanol.

10. The method of claim 1, wherein the third solution has 100 mM salt concentration.

11. The method of claim 1, wherein the third solution has pH 7.0-9.0.

12. The method of claim 1, wherein the third solution comprises 10 mM Tris-HCl, 0.1 mM EDTA, pH 8.0-9.0.

13. The method of claim 1, further comprising a step between steps b and c: flowing a solution BC to wash contaminants of proteins, carbohydrates, and small metabolites from the first layer.

14. The method of claim 13, wherein the solution BC comprises 10-20 mM Tris-HCl, pH 6.0-8.0.

15. The method of claim 1, further comprising a step between steps c and d: flowing a solution CD to wash contaminants of proteins, carbohydrates, and small metabolites from the second layer.

16. The method of claim 15, wherein the solution CD comprises chaotropic salt at a concentration of 2 to 8 M.

17. The method of claim 15, wherein the solution CD comprises ethanol or isopropanol.

18. The method of claim 15, wherein the solution CD comprises 10 mM Tris-HCl, 80% ethanol, pH 6-8.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Homo sapiens

<400> SEQUENCE: 1
agggtcccca ggcctctgat                                        20

<210> SEQ ID NO 2
<211> LENGTH: 22
<212> TYPE: DNA
<213> ORGANISM: Homo sapiens

-continued

```
<400> SEQUENCE: 2
gccactgaca accaccctta ac                                              22
```